Figure 3:
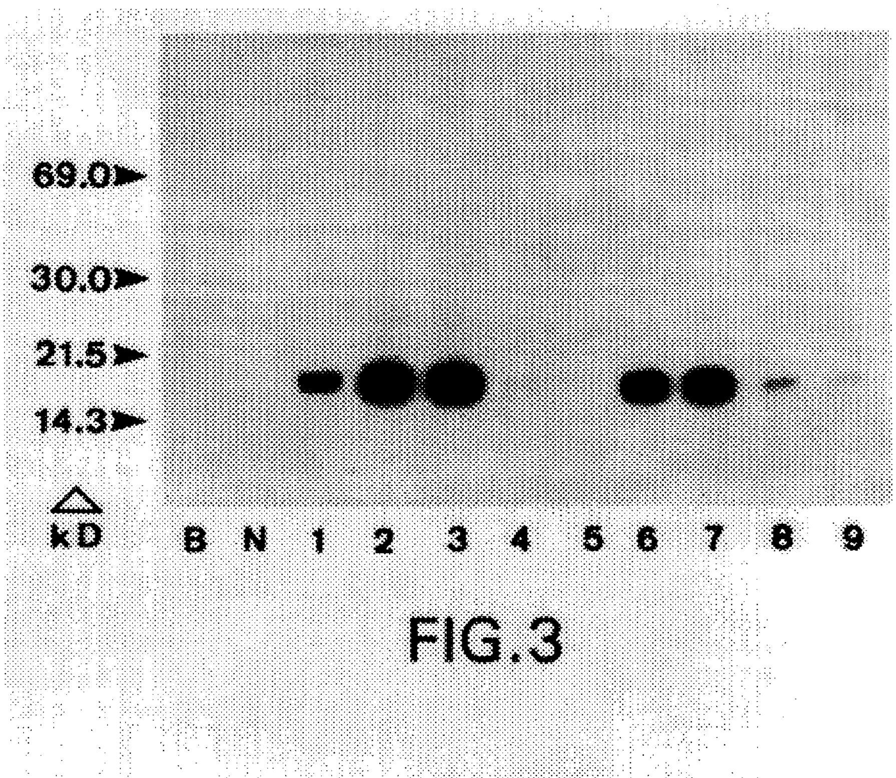

US005693495A

United States Patent [19]

Breiteneder et al.

[11] Patent Number: 5,693,495

[45] Date of Patent: Dec. 2, 1997

[54] ALLERGENS OF ALDER POLLEN AND APPLICATIONS THEREOF

[75] Inventors: Heimo Breiteneder, Vienna; Rudolf Valenta, Theresienfeld; Michael Breitenbach, Vienna; Dietrich Kraft, Vienna; Helmut Rumpold, Vienna; Otto Scheiner, Mariaenzersdorf, all of Austria

[73] Assignee: Biomay Produktions- Und Handelsgesellschaft m.b.H., Austria

[21] Appl. No.: 847,010

[22] PCT Filed: Aug. 6, 1991

[86] PCT No.: PCT/EP91/01479

§ 371 Date: Jun. 1, 1992

§ 102(e) Date: Jun. 1, 1992

[87] PCT Pub. No.: WO92/02621

PCT Pub. Date: Feb. 20, 1992

Related U.S. Application Data

[63] Continuation of Ser. No. 683,831, Apr. 11, 1991, abandoned.

[30] Foreign Application Priority Data

Aug. 8, 1990 [AT] Austria .................................... 1668/90

[51] Int. Cl.$^6$ ............................ A61K 39/36; C12N 15/29

[52] U.S. Cl. .................. 435/69.3; 435/252.3; 435/252.8; 424/184.1; 424/185.1; 424/275.1; 424/276.1; 536/23.1; 536/23.6

[58] Field of Search ............................ 424/88, 91, 184.1, 424/185.1, 275.1, 276.1; 435/69.3, 252.3, 252.8; 514/2; 536/23.1, 23.6

[56] References Cited

FOREIGN PATENT DOCUMENTS

| | | |
|---|---|---|
| A 3147763 | 6/1983 | Germany . |
| WO 89/09260 | 10/1989 | WIPO . |
| 9004025 | 4/1990 | WIPO . |

OTHER PUBLICATIONS

J. Allergy Clin. Immunol, vol. 87, No. 3, Mar. 1991, R. Valenta et al., "Homology of the major birch–pollen allergen, Bet v 1, with the major allergens of alder, hazel, and hornbeam at the the nucleic acid level as determined by cross–hybridization", pp. 677–682.

Biological Abstracts, vol. 86:80603 "Seasonal variation of the conjunctival provocation test, total and specific IgE in children with birch pollen allergy" (1988).

Biosis, 92:91416, J. Allergy Clin. Immunol. 88(6) 1991, Valenta et al. "Recombinant Allergens for Immunoblot Diagnosis of Tree–Pollen Allergy".

The EMBO Journal, vol. 8, No. 7, Jul. 1989, (Eynsham, Oxford, GB) H. Breiteneder et al.: "The gene coding for the major birch pollen allergen Betvl, is highly homologous to a pea disease resistance response gene", pp. 1935–1938.

Allergy, vol. 44, No. 6, Aug. 1989, E. Jarolim et al.: "Ige and IgG antibodies of patients with allergy to birch pollen as tools to define the allergen profile of *Betula verrucosa*", pp. 385–395.

XIV International Congress of Clinical Chemistry, Jul. 23, 1990, 1400–1700, Clinical Chemistry, vol. 36, No. 6, 1990, 0157, Rohac et al., "The Immunological Relationship Between Major Allergens Derived from Pollen of Birch, Alder, Hazel, and Hornbeam, as Defined by Human IgE and Monoclonal Antibodies".

Int. Arch Allergy Appl Immunol 1989:89:410–415, Elsayed et al., "Synthetic Allergenic Epitopes from Amino–Terminal Regions of the Major Allergens of Hazel and Birch Pollen".

Allergy, vol. 43, No. 5, Jul. 1988, Ipsen et al., "Immunotherapy with partially purified and standardized tree pollen extracts", pp. 370–377.

Allergy, vol. 40, No. 7, Oct. 1985, Ipsen et al., "Immunochemical Characterization of Reference Alder (*Alnus glutinosa*) and Hazel (*Corylus avellana*) Pollen Extracts and the Partial Immunochemical Identity between the Major Allergens of Alder, Birch and Hazel Pollens", pp. 510–518.

Journal of Allergy and Clinical Immunology, vol. 81, No. 1, Jan. 1988, 390, Ipsen et al. "Structural Similarities Between Amentifericus Tree Pollen Major Allergens", p. 265.

Chemical Abstracts, vol. 108:202847r "Analysis of rye pollen (*Secale cereale*) allergens by using patients' IgE, immunoprint, Western blot and monoclonal antibodies", 1988, p. 510.

Clinical Experimental Allergy, vol. 20, 1990, Suppl. 1, Meeting 8–11 Jul. 1990, S. d'Abusco et al.: "Characterization of cDNA for Parietaria pollen allergens", p. 48, see abstract OP52.

Chemical Abstracts, vol. 97:53816e "Comparative studies on tree allergens. IV. Evaluation of two commercially available allergen extracts of alder (*Alnus incana*) and birch (*Betula verrucosa*) pollen", 1982, p. 480.

Chemical Abstracts, vol. 104:184481c "Comparative studies on tree pollen allergens. XIII. Partial characterization of the alder (*Alnus incana*) pollen extract by two–dimensional IEF/SDS–PAG electrophoresis combined with electrophoretic transfer and immunoautoradiography", 1986.

(List continued on next page.)

*Primary Examiner*—Laurie A. Scheiner
*Attorney, Agent, or Firm*—Pennie & Edmonds LLP

[57] ABSTRACT

This invention provides recombinant DNA molecules which code for polypeptides that exhibit the antigenicity of an Aln g I allergen of alder, *Alnus sp.*, of a Cor a I allergen of hazel or of a Bet v I allergen of birch and other plants of the order Fageles, and for polypeptides comprising at least one epitope thereof, as well as nucleic acids which under stringent conditions hybridize with such DNA sequences or are derivable from such sequences by degeneracy of the genetic code. In addition, methods are described for using the polypeptides coded by these DNA molecules and their use in the diagnosis or therapy of allergic diseases.

15 Claims, 7 Drawing Sheets

OTHER PUBLICATIONS

Chemical Abstracts, vol. 104:18392e "Immunochemical characterization of reference alder (*Alnus glutinosa*) and hazel (*Corylus avellana*) pollen extracts and the partial immunochemical identity between the major allergens of alder, birch and hazel pollens" 1986, p. 380.
Chemical Abstracts, vol. 107:234414t "Allergologic–immunochemical investigation of various tree pollens. Part I—Characterization of antigen and allergen components in birch, beech, alder, hazel and oak pollens", 1987.
Ipsen, H. and Hansen, O.C. In: *Epitopes of Atopic Allergens*. Sehon, A.H., Kraft, D., Kunkel, G. (eds) (1990) UCB, Brussels, Belgium, pp. 3–8.
Rumpold, et al. In: *Epitopes of Atopic Allergens*. Sehon, A.H., Kraft, D., Kunkel, G. (eds) (1990) UCB, Brussels, Belgium, pp. 26–28.
Valenta, et al. In: *Epitopes of Atopic Allergens*. Sehon, A. H., Kraft, D., Kunkel, G. (eds) (1990) UCB Brussels, Belgium, pp. 73–76.
Florvaag, E. et al. Int. Arch. Allergy Appl. Immunol. 75:300–308 (1984).
Florvaag, E. et al. Int. Arch, Allergy Appl. Immunol. 67:49–56 (1982).
Jarolim, et al. Int. Arch. Allergy Appl. Immunol. 90:54–60 (1989).
Hatton, T. W., Hill, R.D., Ekramoddoullah, A.K.M., Kisil, F.T. and Sehon, A.H., "Molecular Cloning of Kentucky Bluegrass (KBF) Pollen Allergens," J. Allergy Clin. Immunol., (Jan. 1988) 81(1), Zusammenfassung [Abstract] Nr. 58, siehe den ganzen Artikel, Seite [p.] 183.
Hemmens et al., "Allergic response to Birch and Alder Pollen Allergens Influenced by Geographical Location of Allergic Subject", Int. Arch Allergy Appl. Immunol. 87:321–328 (1988).
Berger et al. (eds.) "Molecular Cloning Manual" Methods in Enzymology vol. 152, pp. 316–337, 343–349, 359–371, 451–469 (1987).
Kumar, V. et al. Proc. Natl. Acad. Sci. 87: 1337–1341 (1990).
Bowie, J.V. et al. Science 247: 1306–1310 (1990).
Ellis, R.W. "New Technologies for making vaccines" In: Vaccines Plotkin & Mortimer Eds. W.B. Saunders Co 1988.
Breitemeder, H. et al. EMBO J. 8(7): 1935–1938 (1989).
Sambrook, J. et al. Molecular Cloning Ch 16&17 Cold Spring Harbor Laboratory Press 1989.
Lee, CC et al Science 239: 1288–1291.

*Aln g I*

```
1   2   3   4   5   6   7   8   9   10  11  12  13  14  15  16  17  18  19  20
ATG GGT GTT TTC AAT TAC GAA GCG GAA ACC CCC TCC GTT ATC CCA GCG GCT CGG CTG TTC
Met Gly Val Phe Asn Tyr Glu Ala Glu Thr Pro Ser Val Ile Pro Ala Ala Arg Leu Phe

21  22  23  24  25  26  27  28  29  30  31  32  33  34  35  36  37  38  39  40
AAG GCC TTT ATC CTT GAT GGC GAT AAG CTC CTT CCA AAG GTT GCA CCT GAA GCT GTT AGC
Lys Ala Phe Ile Leu Asp Gly Asp Lys Leu Leu Pro Lys Val Ala Pro Glu Ala Val Ser

41  42  43  44  45  46  47  48  49  50  51  52  53  54  55  56  57  58  59  60
AGT GTT GAG AAC ATT GAA GGA AAT GGA GGG CCT GGA ACC ATC AAG AAG ATC ACC TTT CCC
Ser Val Glu Asn Ile Glu Gly Asn Gly Gly Pro Gly Thr Ile Lys Lys Ile Thr Phe Pro

61  62  63  64  65  66  67  68  69  70  71  72  73  74  75  76  77  78  79  80
GAA GGC AGC CCT TTT AAG TAC GTA AAG GAG AGG GTT GAT GAG GTT GAT CGC GTA AAC TTC
Glu Gly Ser Pro Phe Lys Tyr Val Lys Glu Arg Val Asp Glu Val Asp Arg Val Asn Phe

81  82  83  84  85  86  87  88  89  90  91  92  93  94  95  96  97  98  99  100
AAA TAC AGC TTC AGC GTG ATC GAG GGT GGT GCC GTG GGC GAC GCA CTG GAG AAG GTC TGT
Lys Tyr Ser Phe Ser Val Ile Glu Gly Gly Ala Val Gly Asp Ala Leu Glu Lys Val Cys

101 102 103 104 105 106 107 108 109 110 111 112 113 114 115 116 117 118 119 120
AAC GAG ATC AAG ATA GTG GCA GCC CCT GAT GGA GGA TCC ATC TTG AAG ATC AGC AAC AAG
Asn Glu Ile Lys Ile Val Ala Ala Pro Asp Gly Gly Ser Ile Leu Lys Ile Ser Asn Lys

121 122 123 124 125 126 127 128 129 130 131 132 133 134 135 136 137 138 139 140
TTC CAC ACC AAA GGC GAC CAT GAG ATA AAT GCA GAG CAG ATT AAG ATT GAA AAA GAA AAG
Phe His Thr Lys Gly Asp His Glu Ile Asn Ala Glu Gln Ile Lys Ile Glu Lys Glu Lys

141 142 143 144 145 146 147 148 149 150 151 152 153 154 155 156 157 158 159 160
GCC GTG GGA CTT CTC AAG GCC GTT GAG AGC TAC CTC TTG GCA CAC TCT GAT GCC TAC AAC
Ala Val Gly Leu Leu Lys Ala Val Glu Ser Tyr Leu Leu Ala His Ser Asp Ala Tyr Asn

161
TAA ATTCTGCCTAATTTTGATCAGCTTGCATGTGTTCTTGTCAAGCCATAAATACTGCTTAACTTCGTCTTGCTAATA
End

AATGAAGCTGTTGTAGTCGTTTATGAGTACGTAATAATGACACCAAACATATGGAGCCAATTGCTTATGAATAGAAGTT
AAGTTCTTAAAAAAAAAAAAAAAAAAAA
```

FIG. 1

```
    1            11            21            31            41
5'-TTTAATACGA CTCACTATAG ATCTCCCGGG AAGCTTTTTT TTTTTTTTTT-3'
           T7 Primer     BgIII         HindIII
```

FIG. 2

ALLERGENS OF ALDER POLLEN AND APPLICATIONS THEREOF

This application was filed as PCT international application Ser. No. PCT/EP91/01479, filed Aug. 6, 1991, published as WO92/02621 Feb. 20, 1992, which is a continuation of application Ser. No. 07/683,831, filed Apr. 11, 1991, abandoned.

1. FIELD OF THE INVENTION

The invention provides recombinant DNA molecules which code for polypeptides, and the polypeptides per se, that have at least one epitope of an Aln g I pollen allergen, or a Cor a I pollen allergen or a Bet v I pollen allergen of a tree of the order Fagales, particularly alder, *Alnus sp.*, or the entire Aln g I allergen protein, particularly hazel, *Corylus sp.*, or the entire Cor a I allergen protein, or particularly birch, *Betula sp.*, or the entire Bet v I allergen protein, and exhibit the same or similar anti-genicity as the Aln g I, the Cor a I or the Bet v I allergen. The invention also provides replicable microbial expression vehicles and microorganisms for use in processes for producing such allergenic polypeptides. Methods are provided for the diagnosis and therapy of allergic diseases using the synthetic polypeptides of the invention.

2.BACKGROUND OF THE INVENTION

It has long been known that a type I allergy to pollen proteins is associated with symptoms such as itchy and reddened eyes, running nose, swollen eyelids, coughing and asthmatic conditions. In this respect, the pollens of early-flowering trees of the order Fagales (e.g., birch, hazel, alder and hornbeam) hold an important position. Numerous studies have been carried out to identify and characterize the allergens of these pollens precisely (1–4). Progress with regard to the exact characterization of pollen allergens has been hindered by the heterogeneity of the pollen extracts currently in use. Some eight allergens of alder pollen elicit an IgE response in atopics and one of them, Aln g I, a 17 kD protein, reacts with a majority of the sera of allergic patients as the major allergen (5, 6).

At least 10% of the population suffers from pollen allergies at various times and to varying extent. These allergies are mediated by IgE antibodies which react with pollen proteins. The possibility exists for a therapy for pollen allergies by hyposensitization, i.e., by the regular and slowly increasing administration of the proteins producing the allergy.

Diagnostic methods for allergic diseases, such as radioallergosorbent test (RAST), paper radioimmunosorbent test (PRIST), enzyme-linked immunosorbent assay (ELISA), radioimmunoassays CRIA), immuno-radiometrie assays (IRMA), luminescence immunoassays (LIA), histamine release assays, and IgE immunoblots depend greatly upon the availability of pure nileteens. Protein extracts from pollen isolated from natural sources are difficult to standardize because preparations vary from batch to batch. For example, they may contain unwanted constituents, and/or certain proteins may be lost in the extraction procedure and be missing from the final preparation (7). Clearly, diagnostic tests which employ well defined allergens that can be reprodueibly prepared would be superior to tests which employ raw pollen extracts with an in. sufficiently defined mixture of allergens and other components. Recombinant DNA production of allergenic polypeptides, or altergenic fragments thereof, would allow more reproducible preparations of fliergens of defined content for standardized diagnostic and therapeutic methods.

Allergens may be purified to homogenity from pollen by known protein/chemical methods, for example, by means of affinity chromatography (8). These methods are relatively costly and require pollen as an expensive source for allergens. It would, therefor, be cheaper and more efficient to use recombinant DNA methods to produce an allergenic protein, or fragments of that protein.

Hyposensitization has proved to be an effective therapy in allergic diseases. This therapy consists of parenteral or oral administration of allergens in increasing doses over a fairly long period of time.

3. SUMMARY OF THE INVENTION

The present invention provides recombinant DNA molecules which contain a nucleotide sequence that codes for a polypeptide which exhibits the same or similar antigenic properties as the major allergen, Aln g I, Cor a I or Bet v I of trees of the order Fagales, for example, of alder (*Alnus sp.*), hazel (*Corylus sp.*) or birch (*Betula sp.*) or a polypeptide which comprises at least one epitope of such allergens. The invention provides the complete cDNA sequence of an Aln g I, a Cor a I or a Bet v I allergen and hence the complete deduced amino acid sequences. Additionally, the invention includes (a) nucleotide sequences which hybridize with such a cDNA sequence under high stringency and encode a polypeptide having at least one epitope of an Aln g I, a Cor a I or a Bet v I allergen and (b) nucleotide sequences which can be derived from such allergenic polypeptides by degeneracy of the genetic code. This nucleotide sequence can be expressed as an Aln g I, a Cor a I or a Bet v I allergen, or as a polypeptide which comprises at least one epitope thereof. In a preferred embodiment, this cDNA sequence contains the whole sequence or parts of the sequence set forth in the Sequence Listing as SEQ ID NO.2 for Aln g I, as SEQ.ID NO.10, 13, 16 and 19 for Cor a I and as SEQ ID NO.22 for Bet v I.

As concerns their IgE binding: pollens of birch, alder, hazel and hornbeam possess similar major allergens which—so far as is known—exhibit a high degree of hornology on the amino acid level. The present invention therefore relates not only to an Aln g I allergen of alder, or Cor a I of hazel or Bet v I of birch, but as well to Aln g I, Cor a I or Bet v I pollen allergens of other species which are coded by DNA allergen under stringemt conditions or can be derived from such polypeptide allergens by degeneracy of the genetic code.

Hybridization of a polynucleotide with another polynucleotide under stringent conditions requires at least a 60% identity between such polynucleotides at the nucleic acid level.

Such stringent conditions entail washing of hybridized nitrocellulose filters as follows:

(a) For DNA/DNA and DNA/RNA hybridizations: A temperature of 55° C., a salt concentration of 150 mM NaCl and 15 mM $Na_3$ citrate at pH 7,0, and a SDS (Sodium Dodecyl Sulfate) detergent at a concentration of 0,1% (w/v).

(b) For oligodexynucleotide/DNA hybridizations: A temperature of 55° C., a salt concentration of 1M NaCl and 10 mM $Na_3citrate \times 2H_2O$ at pH 7,0, and a SDS (Sodium Dodecyl Sulfate) detergent at a concentration of 0,5% (w/v). In this context "oligodeoxynucleotide" refers to an oligomer of a single-stranded DNA of up to 100 nucleotides in length.

In addition, this invention provides expression plasmids that contain a nucleotide sequence as described above and host cells which harbor these expression plasmids.

This invention also provides compositions containing synthetic polypeptides which exhibit the antigenicity of parts or of the whole of an alder Aln g I allergen or of allergens of other plants which, because of a high degree (at least 50%) of amino acid homology (9), exhibit antigenie cross-reactivity to parts or to all of an alder Aln g I allergen, i.e., antibodies or cellular antigen binding sites which are actually directed to alder Aln g I allergen are likewise able to bind to these molecules. These synthetic polypeptides include fusion and nonfusion polypeptides which contain a polypeptide portion that possesses the antigenicity of a part or of all of an alder polypeptid which contain a polypeptide portion that possesses the antigenicity of a part or of all of an Aln g I or a Cor a I or a Bet v I allergen. The method for preparing such synthetic polypoptides comprises the steps of culturing of prokaryotic or eukaryotic host cells which contain an expression plasmid described above and purification of the synthetic polypeptide(s) from the culture.

The term "synthetic" here alternatively includes polypeptides which are prepared by cloning and expression of the nucleotide sequences described here or by chemical synthesis of polypeptides encoded by these nucleotide sequences.

The synthetic polypeptides which are produced according to this invention exhibit antigenicity the same as or similar to the native allergen. As shown below, a cDNA clone coding for an alder Aln g I, a hazel Cor a I or a birch Bet v I can be used to produce a nonfusion polypeptide which reacts with IgE in the sera of allergic persons. It is therefore possible to use this polypeptide as an antigen in diagnostic tests (such as RAST, PRIST, EISA, RIA, IRMA, LIA, histamine release assays and IgE immunoblots known in the art and referred to above), as a component of prophylactic or therapeutic agents in hyposensitization therapy, and as a component in any kind of in vivo diagnostic procedure such as bronchial, conjunctival, dermal, nasal and oral provocation and skin tests.

In particular, the synthetic allergens east be used as diagnostic reagents in vitro and in vivo, since their antigenicity corresponds to that of the native Aln g I pollen allergens and they are therefore able to bind IgE of sera of persons suffering from Aln g I pollen allergy. In the same way, the antigenicity corresponds to that of the native Cor a I or Bet v I pollen allergens and they are also able to bind IgE of sera of sensitive or allergic patients.

It is therefore one of the objects of the present invention to provide a method for the preparation of pollen allergens, in particular for Aln g I, Cor a I or Bet v I allergens, so as to have this family of allergens available for diagnostic tests for detection of the corresponding allergy and, alternatively, for hyposensitization therapy.

As main epitopes capable of modifying T-cell response the following amino acid sequences were found:

GlyValPheAsnTyrGlu
PheIleLeuAspGlyAspLysLeu
AlaIleSerSerValGluAsnIle
GlyAsnGlyGlyProGlyThrIleLysLysIleSerPhe
LysTyrValLysAspArgValAspGluValAsp
LeuLeuArgAlaValGluSerTyrLeuLeuAlaHisSer.

All these sequences are present in all said allergens, i.e. Aln g I, Cor a I and Bet v I.

4. BRIEF DESCRIPTION OF THE FIGURES

The following figures and description aid in understanding the field and scope of the invention.

FIG. 1 shows a cDNA (665 nucleotides, SEQ ID NO.1) encompassing the nucleotide sequence encoding an Aln g I allergen of alder. The cDNA sequence consists of a coding region of 483 nucleotides (including the initation and termination codons), a 3' noncoding region of 162 nucleotides and a poly-A tail of 20 nucleotides. The deduced amino acid sequence of alder Aln g I polypeptide is indicated in FIG. 1 under the respective condons. The complete protein has 160 (SEQ ID NO.3) amino acids (including the methionine of the initiation codon).

FIG. 2 shows the nucleotide sequence of the BP-A primer (SEQ ID NO.4) that was used for synthesis of the first cDNA strand. The recognition sequences of the restriction enzymes BglII (nucleotides 19–24) and HindIII (nucleotides 31–36) are underlined. The sequence of T7 primer (nucleotides 4–17), which was used as primer for the PCR amplification of Aln g I and is the constituent of BPA, is likewise indicated.

FIGS. 3–10 show Immunoblot analysis of isoforms of the major hazel pollen allergen Cor a I as recombinant nonfusion proteins, in particular FIG. 3: An identical set of patients' sera was used to characterize the Cor a I isoforms (lanes 1–9). In FIG. 3, the Cor a I isoform expressed by the DNA sequence of SEQ ID NO:9 was characterized.

Lane B: buffer control without addition of patients' sera.

Lane N: a pool of non-allergic normal human sera.

IgE antibodies from the allergic patients' sera, which bound to the isoform expressed by the DNA of SEQ ID NO:9, was detected by $^{125}$I labeled rabbit-anti human IgE and showed reactivity with IgE from allergic patients' sera. All isoforms were able to bind IgE, although their individual binding pattern may differ from patient to patient.

Figure 4:
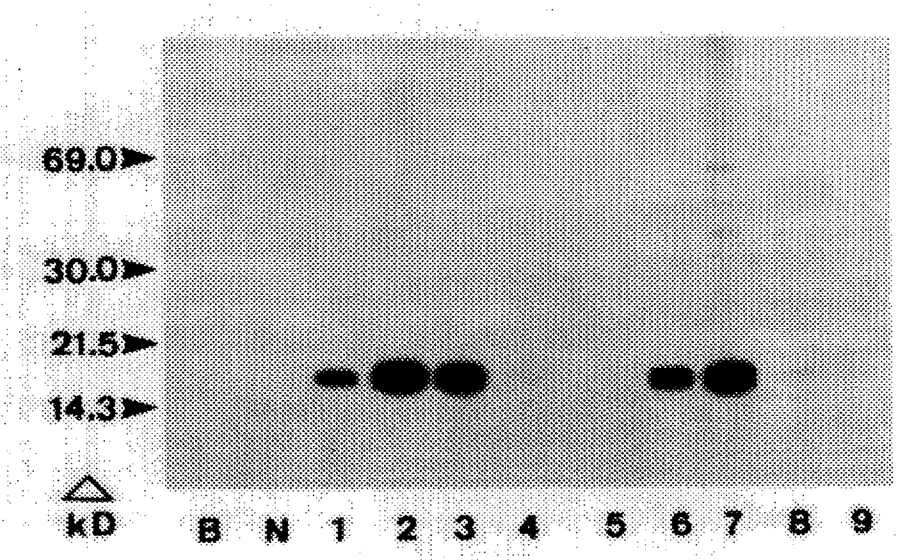

FIG. 4: The Cor a I isoform expressed by the DNA sequence of SEQ ID NO:12 was characterized.

Lane B: buffer control without addition of patients' sera.

Lane N: a pool of non-allergic normal human sera.

IgE antibodies from the allergic patients' sera, which bound to the isoform expressed by the DNA of SEQ ID NO:12, was detected by $^{125}$I labeled rabbit-anti human IgE and showed reactivity with IgE from allergic patients' sera. All isoforms were able to bind IgE, although their individual binding pattern may differ from patient to patient.

Figure 5:
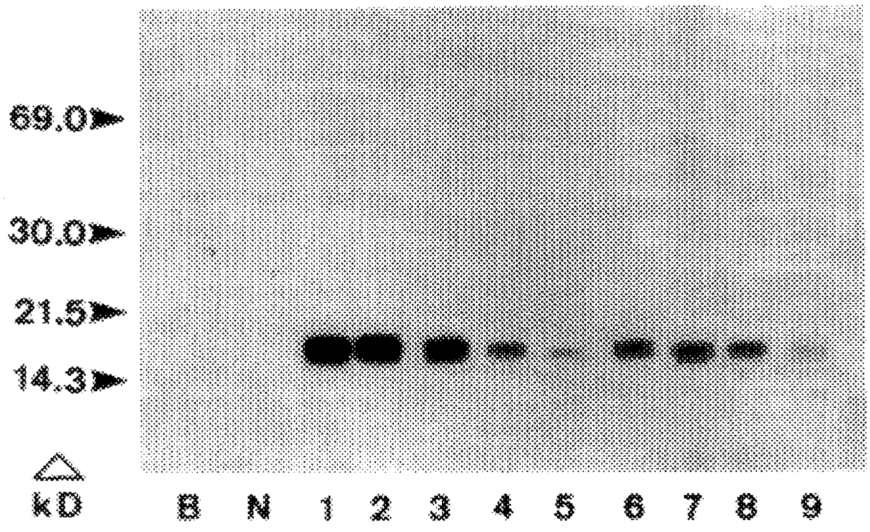

FIG. 5: The Cor a I isoform expressed by the DNA sequence of SEQ ID NO:15 was characterized.

Lane B: buffer control without addition of patients' sera.

Lane N: a pool of non-allergic normal human sera.

IgE antibodies from the allergic patients' sera, which bound to the isoform expressed by the DNA of SEQ ID NO:15, was detected by $^{125}$I labeled rabbit-anti human IgE and showed reactivity with IgE from allergic patients' sera. All isoforms were able to bind IgE, although their individual binding pattern may differ from patient to patient.

Figure 6:
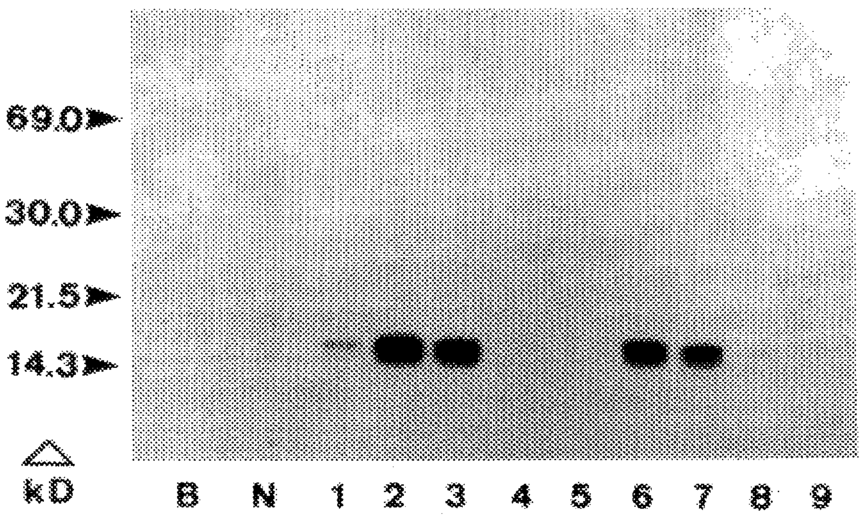

FIG. 6: The Cor a I isoform expressed by the DNA sequence of SEQ ID NO:18 was characterized.

Lane B: buffer control without addition of patients' sera.

Lane N: a pool of non-allergic normal human sera.

IgE antibodies from the allergic patients' sera, which bound to the isoform expressed by the DNA of SEQ ID NO:18, was detected by $^{125}$I labeled rabbit-anti human IgE and showed reactivity with IgE from allergic patients' sera. All isoforms were able to bind IgE, although their individual binding pattern may differ from patient to patient.

Figure 7:
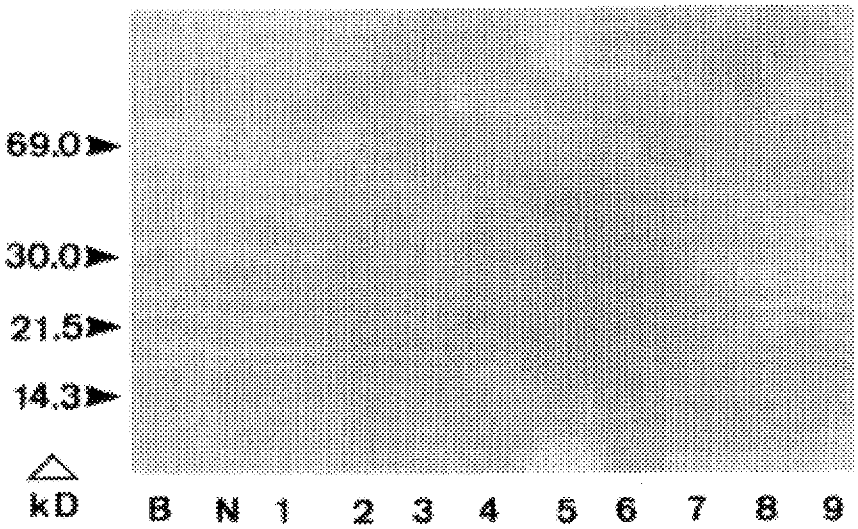

FIG. 7: An identical set of experiments was performed using *E.coli* JM 105 transformed with the plasmid pKK 223.3 without any cDNA insertion. No bound IgE could be detected.

Figure 8:
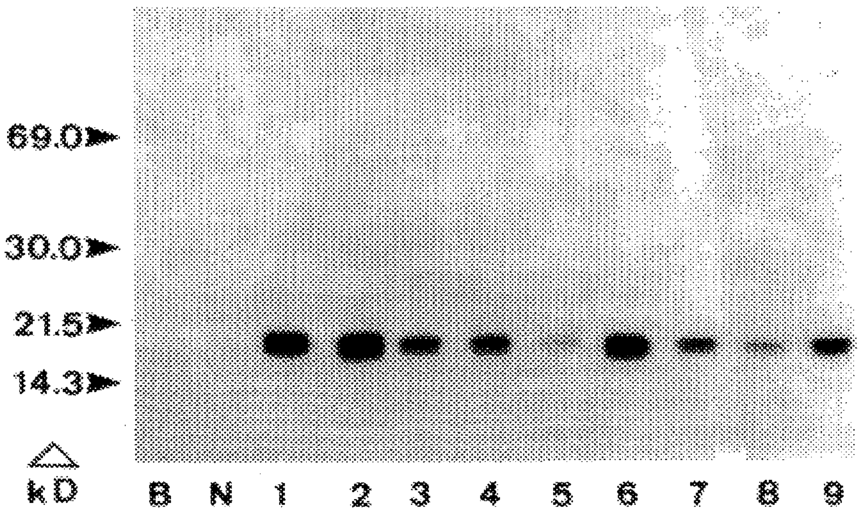

FIG. 8: Likewise the cDNA fragment whose sequence is shown in SEQ ID NO.1 was ligated into the expression plasmid pKK 223.3. The protein corresponding to the coding region (see SEQ ID NO.2 and SEQ ID NO.3) was expressed in *E.coli* JM 105 and tested with the identical set of patients' sera as above. rAln g I was able to bind IgE from these patients' sera in each case (lanes 1–9). In lanes B (buffer control, no patients' sera) and N (a pool of sera from non allergic individuals) no binding could be observed.

Figure 9:
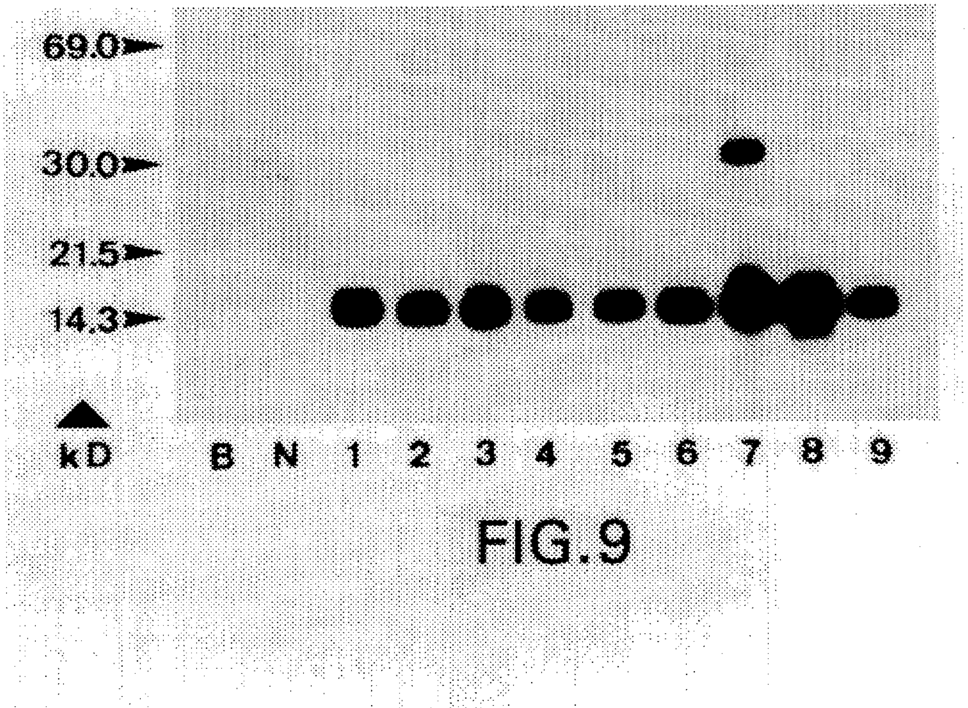

FIG. 9: This represents the quality control of the patients' sera used in the above experiments. The very same set of sera was tested on separated and blotted proteins from an aqueus extract of birch pollen. IgE from every single serum bound strongly to the major allergen of birch pollen, Bet v I (lanes 1–9). No binding could be observed for the buffer control (lane B) and the pool of sera from non allergic individuals.

Figure 10:
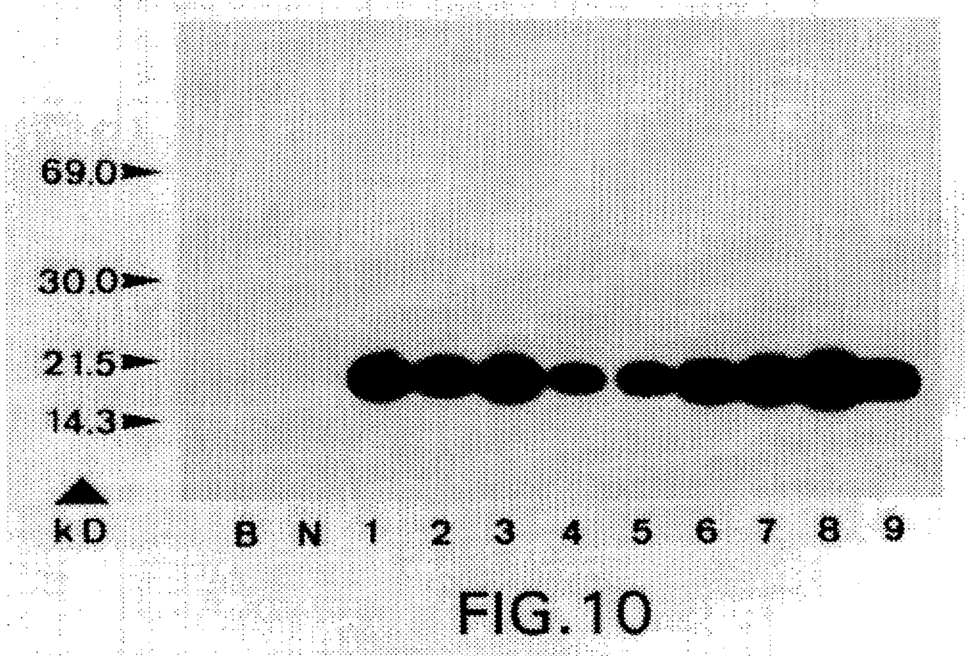

FIG. 10: Furthermore the same sera were tested on rBet v I and showed exactly the same strong reactivity with the recombinant nonfusion protein.

Figure 11:
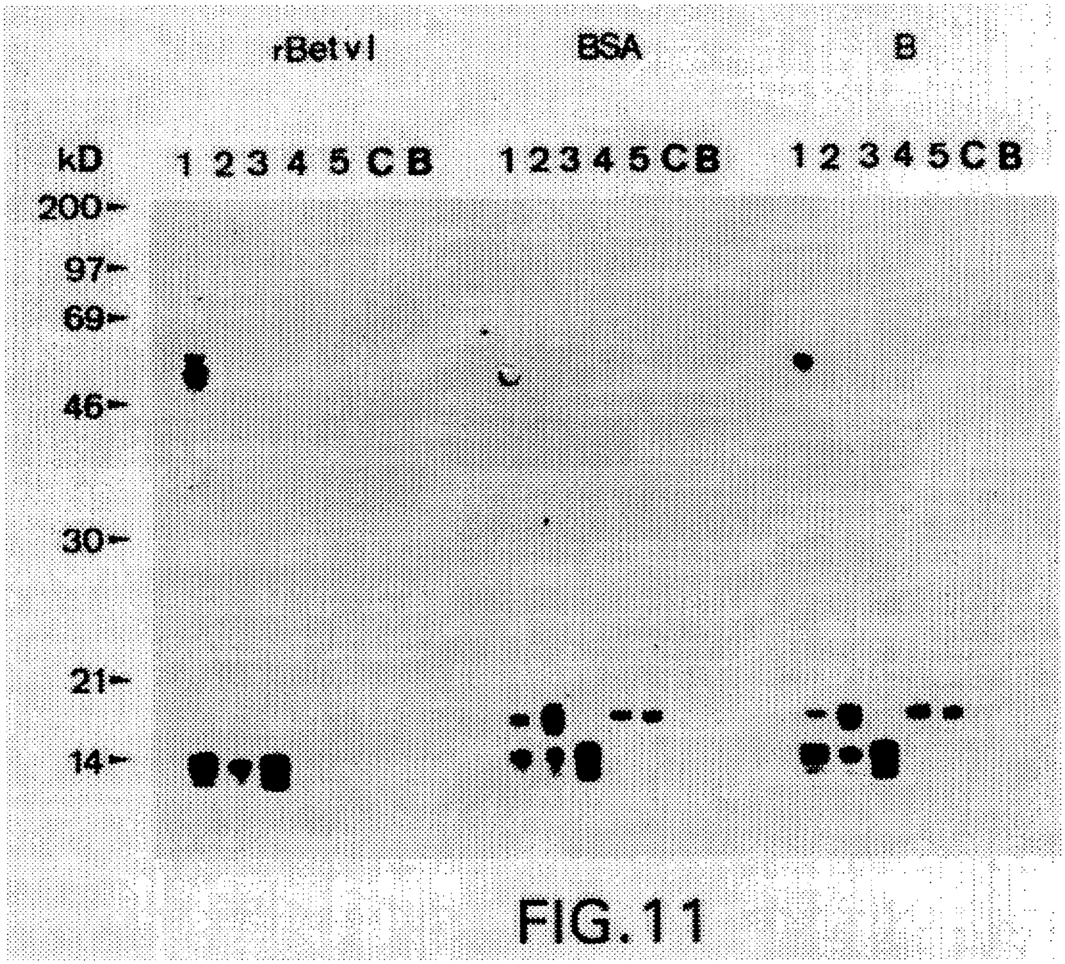

FIG. 11: Inhibition experiment showing the capacity of rBet v I to bind IgE from tree pollen allergic patients' sera and thus to prevent the IgE from further binding to the corresponding hazel pollen allergen Cor a I. 1 ml each of a 1:10 dilution of birch pollen allergic individuals' sera (1–5), of a serum pool of non allergic individuals (6), and buffer without the addition of serum (7) was incubated over night at 4° C. with the addition of 5 μg of rBet v I (panel 1), 5 μg of BSA (panel 2), or buffer only (panel 3). These samples were used to probe a Western blot of SDS-PAGE-separated hazel pollen proteins. In the case where rBet v I had been added no IgE binding to the 17 kD Cor a I could be observed. The addition of bovine serum albumin (BSA) or buffer without addition of a protein could not inhibit the binding of patients' IgE to the hazel Cor a I.

5. EXAMPLES

5.1. Poly A+ RNA Isolation From Pollen and Synthesis of the First cDNA Strand Polyadenylated (polyA+) mRNA was isolated from ripe alder pollen (Allergon AB, Engelsholm,Sweden) (1). Using this, the first strand of cDNA was synthesized as follows:

2 μl 10×buffer (480 mM Tris (hydroxymethyl) aminomethane (Tris), 60 mM $MgCl_2$, 400 mM KCl, pH 4,8)

2 μl 10 mM dithiothreitol (DTT)

1 μl primer BP-A (100 ng/μl, nucleotide sequence of FIG. 2) (SEQ ID NO.4)

2 μl 25 mM deoxynucleoside triphosphates (dNTPs), i.e. 25 mM each of dATP, dCTP, dGTP, dTTP (Pharmacia, Uppsala, Sweden)

11 μl $H_2O$

1 μl poly A+RNA (3 μg)

1 μl AMV reverse transcriptase (United States Biochemical Corporation (USB), Cleveland, Ohio, USA)=32 Units.

This reaction, with a total volume of 20 μl, was incubated for 2 hours at 42° C., then diluted 1:1 with 1×TE buffer (10 mM Tris, 1 mM ethylenediamine tetraacetic acid (EDTA), pH 8,0) and stored at 4° C.

5.2 Polymerase Chain Reaction (PCR)

PCR was carried out on the hybrid RNA-DNA molecules prepared in Section 5.1. A mixture of the following two oligodeoxynucleotides was used as primer for the 5'-end of the molecules:

No. 2482 (SEQ ID NO.5)

5'-GTT TIC AAT TAC GAA GCG GAA AC-3'

No. 2490 (SEQ ID NO.6)

5'-GTT TTC AAT TAC GAA GCG GAG AC-3'

The nueleotide sequences of these oligodeoxynueleotides were derived from the N-terminal amino acid sequence of alder Aln g I partially determined by Edman degradation and follwing the codon usage of birch (*B. verrucosa*).

T7 primer (SEQ ID NO.7) (Pharmacia), which is likewise a constituent of the BP-A primer, was used as primer for the 3' end of the molecules. The following mixture was used for the reaction:

2.5 μl of the reaction mixture in Section 5.1

5.0 μl 10×PCR buffer (400 mM KCl, 10 mM $MgCl_2$, 10% gelatin, 100 mM Tris, pH 8.3)

2.0 μl T7 primer (SEQ ID NO.7) (Pharmacia)=20 pmol 4.0 μl primer mix in equal parts of No. 2482 (SEQ ID NO.5) and 2490 (SEQ ID NO.6)=100 pmol 2.5 μl 2 mM dNTPs (Pharmacia)

1.5 μl 100 mM $MgCl_2$ 32.5 μl $H_2O$ (to 50 μl)

Addition of 1 unit Taq DNA polymerase (USB). The reaction mixture was incubated for 30 seconds at 93° C., for 30 seconds at 55° C. and for 1 minute at 72° C. This cycle was run through 30×in all. Finally, the reaction mixture was kept at 72° C. for another 10 minutes.

5.3 Cloning of the PCR Fragment and Sequencing

The DNA fragment synthesized in Section 5.2 was isolated from a 1,5% agarose gel by means of DEAE paper (10). This fragment was then kinased at the 5'-end.

a) Kinasing

10 μl DNA (=500 ng Aln g I DNA)

2.5 μl 10×T4 polynucleotide kinase buffer (Boehringer, Mannheim, Germany)

7.0 μl $\gamma$-$^{32}$P-ATP, 10 mCi/ml (Amersham, Little Chalfont, England 4.5 μ,l $H_2O$ 1.0 polynucleotide kinase (Boehringer)

The reaction mixture was incubated for 20 minutes at 37° C. After that another addition of 1 μl polynucleotide kinase was made and the mixture was incubated for 60 minutes at 37° C.

b) Klenow fill-in reaction:

To the above reaction mixture was added:

1 μl 2 mM dNTPS (Pharmacia)

1 μ,l Klenow Fragment (=2 units)

The Kinased and filled-in DNA fragment was purified by way of a Nick™ Column (Pharmacia) and was then precipitated with ethanol and sodium acetate (9).

c) BglII digestion of fragment:

Several restriction enzyme sites were added at the 3'-end to the Aln g I sequence through the use of the BP-A oligodeoxynucleotide (FIG. 2; SEQ ID NO.4) in the PCR. The BglII site in this sequence was selected for cleavage with the restriction enzyme, BglII, to ligate the fragment in the corresponding BglII site of pBluescript® plasmid (Stratagene, LaJolla, Calif., USA). Due to the Klenow reaction, blut ends had already been produced at the 5'-end of the sequence. All the DNA precipitated in Section 5.3b was dissolved in 2 μl 10×BglII buffer (Boehringer). 17 μl $H_2O$ and 1 μl BglII (11 units) were added. The reaction mixture was incubated for 1.5 hours at 37° C. The fragment so cut was eluted from a 1.5% agarose gel by means of DEAE paper (10).

d) Ligation of the DNA fragment in pBluescript® KS+ plasmid:

pBlueseript® KS+ plasmid (Stratagene) was selected as cloning vector and cut with the restriction enzymes EcoRV (supplies flush ends; the 5'-end of the Aln g I fragment is ligated to these) and BamHI (supplies staggered ends compatible with BglII; the 3'-end of the Aln g I fragment is ligated to these). The phosphate groups at the 5'-ends of the plasmid were removed by alkaline phosphatase (12) to prevent non-specific religation of the vector.

Ligation of Aln g I fragment in pBluescript® KS+ plasmid:

20 ng DNA from Section 5.3c dissolved in 10 µl $H_2O$ 2.0 µl 10×ligation buffer (200 mM Tris, 50 mM $MgCl_2$, 50 mM DTT, 500 µg/ml bovine serum albumin; pH 7.6)

1.0 µl 10 mM ATP 3.0 µl pBluescript® KS+ cut with EcoRV and BamHI (=50 ng)

4.0 µl $H_2O$ 1.0 µl T4 DNA ligase Boehringer (=3 units)

This reaction was incubated for 4 hours at room temperature.

e) Transformation of competent *E.coli* host cells:

Transformation was carried out in *E.coli* XL1-Blue cells (Stratagene) (13). The selection of positive clones was carried out on ampicillin-containing (100 µg/ml) culture plates by means of the blue-white indication system (14).

f) Sequencing of Aln g I DNA:

Sequencing of Aln g I DNA was carried out by means of a T7 sequencing kit (Pharmacia), according to the manufacturer's instructions.

5.4 Expression of Aln g I DNA and Detection of IgE Binding of the Resulting Proteins a) The DNA insert from the pBluescript® KS+ vector, which contains the coding sequence for Aln g I, was subjected to mutagenesis according to Kunkel et al (15). To complete the Aln g I sequence at the 5'-end and provide k with the ATG codon and an additional EcoRI site, the following oligodeoxynucleotide was synthesized (SEQ ID NO.8): 5'-CTT CGT AAT TGA AAA CAC CCA TGA ATT CCG ATA CCG TCG A-3' and used for mutagenesis. This enabled the Aln g I sequence to be ligated, in the correct orientation, by means of the EcoRI site at the 5'-end and by means of the HindIII site at the 3'-end of the gene in the expression plasmid pKK 223-3 (Pharmacia). *E.coli* K12 JM105 cells (thi, rpsL, endA sbcB15, hsdR4, delta. (lacpro AB)/F', thraD36, proAB, lacIZ delta M15) were transformed with this plasmid. After protein, synthesis was effected, the bacteria cells were harvested and broken up with liquid nitrogen. The lysate was separated on a SDS polyacrylamide gel. Detection of recombinant Aln g I nonfusion protein was done by means of immunoblot. IgE in the sera of allergic patients was bound by the recombinant Aln g I. Detection of bound IgE was effected by $^{125}$I-labeled antihuman IgE (Pharmacia).

b) The DNA insert in pBluescript® KS+ plasmid, which contains the sequence coding for Aln g I, was ligated by means of EcoRI linkers (Boehringer) in the expression plasmids pEX A, pEX B and pEX C (16), which shift the reading frame of the insert one nucleotide each time. In this way, in one case the correct reading frame for AIn g I was obtained and the production of a recombinant Aln g I fusion protein was induced. The capability of this recombinant Aln g I fusion protein to bind IgE in sera of patients allergic to alder pollen was shown, by means of immunoblot. Detection of bound IgE was effected by $^{125}$I-labeled antihuman IgE (Pharmacia).

An analogous method was applied for the cloning and expressing of Cor a I.

5.5 Expression of Cor a I DNA and Detection of IgE Binding of the Resulting Protein The cDNA fragments whose sequences are shown in SEQ ID NO.9, 12, 15 and 18 were ligated into the expression plasmid pKK 223.3 (Pharmacia LKB Biotechnology, Uppsala, Sweden). The proteins corresponding to the coding region (see SEQ ID NO.10, 13, 16 and 19) of these fragments were expressed in *E.coli* JM 105 transformed with the respective recombinant plasmids. Cultures were grown until the $OD_{600}$ reached 0.4. Isopropyl-β-D-galaetopyranoside was then added to a final concentration of 0.5 mM and the cultures grown at 37° C. over 3.5 hours for expression of recombinant non-fusion proteins. Bacterial cells were harvested by centrifugation, taken up in 50 mM Tris-HCl buffer, pH 7.5, containing 220 mM NaCl and the cells were disrupted by a freezethaw cycle. The supenatant containing the recombinant non-fusion proteins was loaded onto a 15% SDS-PAGE. The separated proteins were transferred to a nitrocellulose filter. IgE-binding proteins were detected by the use of allergic patients' sera.

The results are shown in FIGS. 3–6.

5.6 Test of Reaction of T-cell Epitopes

Peripheral blood was collected from birch pollen allergic patients who showed igE reactivity to Bet v I exclusively, as demonstrated by Western Blot. Peripheral mononuclear cells (PBMC; the white blood cell fraction containing the lymphocytes) were isolated by density gradient centrifucation. Allergen specific T-cells were enriched by culturing PBMC in presence of Bet v I. After a cloning procedure, T-cell clones (TCC) were proved to react with the complete Bet v I molecule by a proliferation assay, showing that in presence of the specific allergen a proliferation occurs, which is at least 10-fold higher than the autoproliferative activity of the TCC, as measured by $^3$H-Thymidine incorporation. Two Bet v I specific TCC isolated from atopic donors reacted in the same way with the above mentioned peptides as with the whole Bet v I molecule, proving that these peptides represent or contain the relevant T-cell epitopes.

| TCC | TCC + FC | TCC + FC + Bet v I | TCC + FC + PEPTIDE | |
|---|---|---|---|---|
| 443 | 960 | 30516 | 31580* | cpm |
| 160 | 508 | 21218 | 23309** | cpm |

FC: feeder cells
cpm: counts per minute
*peptide: LLRAVESYLLAHS
**peptide: KYVKDRVDEVD

6. METHODS OF ADMINISTRATION

The present invention covers the use of the recombinant or synthetic polypeptide allergens to treat a mammal using such polypeptides alone or in combination with any pharmaceutically acceptable carriers or diluents, in accordance with standard pharmaceutical practice.

The method of treatment involves the administration of such a polypeptide allergen or parts thereof by any route of administration, that is bronchial, conjunctival, dermal, enternal, nasal, oral or vaginal. A range of from 1 picogram to 10 milligrams per application can be used. The diluents and carriers can be chosen by those skilled in the art according to commonly accepted galenic procedures. Like diagnostic methods, it requires pure and well defined allergens. The use of purified recombinant allergens or synthetic peptides would greatly reduce the risk of sensitizing patients to unwanted components.

7. REFERENCES

The references cited in the above specification are:

1. Breiteneder, H., Pattenburger, K., Bito, A., Valenta, R., Kraft, D., Rumpold, H., Scheiner, O., Breitenbach, M. (1989). The gene coding for the major birch pollen allergen, Bet v I, is highly homologous to a pea resistance response gene. EMBO J., 8: 1935–1938.

2. Ipsen, H. and Hansen, O. C. (1990). Physiochemical and immunological characteristics of allergens. In: Epitopes of atopic allergens Sehon, A. H., Kraft, D., Kunkel, G. (eds) UCB, Brussels, Belgium, pp 3–8.

3. Rumpold, H., Rohac, M., Bohle, B., Breitenbach, M., Scheiner, O., Kraft, D. (1990). The relationship of Bet v I epitopes recognized by patients' IgE and monoclonal anti-Bet v I antibodies. In: Epitopes of atopic allergens. Sehon, A. H., Kraft, D., Kunkel, G. (eds) UCB, Brussels, Belgium, pp 26–28.

4 Valenta, R., Breiteneder, H., Pettenburger, K., Breitenbach, M., Scheiner, O., Kraft, D. (1990). RNA- and DNA-sequence similarities of the major allergens of birch, alder, hazel and hornbeam pollens. In: Epitopes of atopic allergens. Sehon, A. H., Kraft, D., Kunkel, G. (eds) UCB Brussels, Belgium, pp 73–76.

5. Florvaag, E. and Elsayed, S. (1984). Comparative studies on tree pollen allergens. VIII. Immunological properties of the alder (*Alnus incana*) pollen extract. Int. Arch. Allergy Appl. Immunol. 75: 300–308.

6. Florvaag, E., Elsayed, S., Apold, J. (1982). Comparative studies on tree pollen allergens. II. Isolation of alder (*Alnus incana*) pollen allergens: purification and some characteristics of the major allergen pI 4.78. Int. Arch. Allergy Appl. Immunol. 67: 49–56.

7. Thomas, W. R., Chua, K. Y., Greene, W. K., and Stewart, G. A. (1990). Recombinant mite allergens. In: Epitopes of atopic allergens. Sehon, A. H., Kraft, D., and Kunkel, G. (eds). UCB Institute of Allergy, Brussels.

8. Jarolim, E., Tejkl, M., Rohac, M., Schlerka, G., Breitenbach, M., Scheiner, O., Kraft, D., and Rumpold, H. (1989). Monoclonal antibodies against birch pollen allergens; characterization by immunoblotting and use for single step affinity purification of the major allergen BetvI. Int. Arch. Allergy Appl. Immunol. 90: 54–60.

9. Needleman, S. B., Wunsch, C. D. (1970). A general method applicable to the search for similarities in the amino acid sequence of two proteins. J. Mol. Biol. 48: 443–453.

10. Ausubel, F.M. (ed) (1987). Current Protocols in Molecular Biology. Green Publishing Associates and Wiley Intescience: John Wiley and Sons, New York. Unit 2.6.

11. Ibid., Unit 2.1.

12. Ibid., Unit 3.10.

13. Ibid., Unit 1.8.

14. Ibid., Unit 1.

15. Kunkel, T. A., Roberts, J. D. Zakour, R. A. (1987). Rapid and efficient site-specific mutagenesis without phenotypic selection. In: Methods in Enzymology Vol. 154. Wu, R. and Grossman, L. (eds) Academic Press, Inc. pp 367–382.

16. Nagair K., Thφgersen, H. C. (1984). Generation of δ-globin by sequence-specific proteolysis of a hybrid protein produced in *Esherichia coli*. Nature 309: 810–812.

We claim:

1. A recombinant DNA molecule encoding a Cor a I allergen, wherein said allergen has the amino acid sequence of SEQ ID NO:17.

2. A recombinant DNA molecule wherein said DNA molecule has the nucleotide sequence of SEQ ID NO:16.

3. A method for producing a Cor a I allergen, comprising the steps of: (a) culturing prokaryotic or eukaryotic host cells comprising Cor a I encoding DNA according to claim 2 under such conditions that said Cor a I allergen is expressed by said host cells and (b) recovering said allergen.

4. A replicable prokaryotic or eukaryotic expression vehicle comprising the DNA molecule according to claim 1.

5. A prokaryotic or eukaryotic host cell comprising the expression vehicle according to claim 4.

6. A host cell according to claim 5 wherein the host cell is *Escherichia coli.*

7. A recombinant DNA molecule wherein said DNA molecule has the nucleotide sequence of SEQ ID NO:15.

8. A method for producing a Cor a I allergen, comprising the steps of: (a) culturing prokaryotic or eukaryotic host cells comprising Cor a I encoding DNA according to claim 7 under such conditions that said Cor a I allergen is expressed by said host cells and (b) recovering said allergen.

9. A replicable prokaryotic or eukaryotic expression vehicle comprising the DNA molecule according to claim 7.

10. A prokaryotic or eukaryotic host cell comprising the expression vehicle according to claim 9.

11. A host cell according to claim 10 wherein the host cell is *Escherichia coli.*

12. A method for producing a Cor a I allergen, comprising the steps of: (a) culturing prokaryotic or eukaryotic host cells comprising Cor a I encoding DNA according to claim 1 under such conditions that said Cor a I allergen is expressed by said host cells and (b) recovering said allergen.

13. A replicable prokaryotic or eukaryotic expression vehicle comprising the DNA molecule according to claim 1.

14. A prokaryotic or eukaryotic host cell comprising an expression vehicle according to claim 13.

15. A host cell according to claim 14 wherein the host cell is *Escherichia coli.*

* * * * *

UNITED STATES PATENT AND TRADEMARK OFFICE
CERTIFICATE OF CORRECTION

PATENT NO. : 5,693,495

DATED : Dec. 2, 1997

INVENTOR(S) : Breiteneder et al.

It is certified that error appears in the above-identified patent and that said Letters Patent is hereby corrected as shown below:

On the title page, please delete the Related U.S. Application Data and insert thereof: --Continuation-in-part of Ser. No. 683,831, filed on Apr. 11, 1991, abandoned.--

In column 34, line 30, for the claim reference numeral 1, should read --2--.

Signed and Sealed this

Eighteenth Day of August, 1998

Attest:

BRUCE LEHMAN

*Attesting Officer* *Commissioner of Patents and Trademarks*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 665 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Alder (Alnus sp.)

( x i ) SEQUENCE DESCRIPTION: SEQ ID NO:1:

```
ATGGGTGTTT TCAATTACGA AGCGGAAACC CCCTCCGTTA TCCCAGCGGC TCGGCTGTTC    60

AAGGCCTTTA TCCTTGATGG CGATAAGCTC CTTCCAAAGG TTGCACCTGA AGCTGTTAGC   120

AGTGTTGAGA ACATTGAAGG AAATGGAGGG CCTGGAACCA TCAAGAAGAT CACCTTTCCC   180
```

-continued

```
GAAGGCAGCC CTTTTAAGTA CGTAAAGGAG AGGGTTGATG AGGTTGATCG CGTAAACTTC 240
AAATACAGCT TCAGCGTGAT CGAGGGTGGT GCCGTGGGCG ACGCACTGGA GAAGGTCTGT 300
AACGAGATCA AGATAGTGGC AGCCCCTGAT GGAGGATCCA TCTTGAAGAT CAGCAACAAG 360
TTCCACACCA AAGGCGACCA TGAGATAAAT GCAGAGCAGA TTAAGATTGA AAAAGAAAAG 420
GCCGTGGGAC TTCTCAAGGC CGTTGAGAGC TACCTCTTGG CACACTCTGA TGCCTACAAC 480
TAAATTCTGC CTAATTTTGA TCAGCTTGCA TGTGTTCTTG TCAAGCCATA AATACTGCTT 540
AACTTCGTCT TGCTAATAAA TGAAGCTGTT GTAGTCGTTT ATGAGTACGT AATAATGACA 600
CCAAACATAT GGAGCCAATT GCTTATGAAT AGAAGTTAAG TTCTTAAAAA AAAAAAAAAA 660
AAAAA 665
```

( 2 ) INFORMATION FOR SEQ ID NO:2:

( i ) SEQUENCE CHARACTERISTICS:
( A ) LENGTH: 480 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Alder (Alnus sp.)

( x i ) SEQUENCE DESCRIPTION: SEQ ID NO:2:

```
ATGGGTGTTT TCAATTACGA AGCGGAAACC CCCTCCGTTA TCCCAGCGGC TCGGCTGTTC 60
AAGGCCTTTA TCCTTGATGG CGATAAGCTC CTTCCAAAGG TTGCACCTGA AGCTGTTAGC 120
AGTGTTGAGA ACATTGAAGG AAATGGAGGG CCTGGAACCA TCAAGAAGAT CACCTTTCCC 180
GAAGGCAGCC CTTTTAAGTA CGTAAAGGAG AGGGTTGATG AGGTTGATCG CGTAAACTTC 240
AAATACAGCT TCAGCGTGAT CGAGGGTGGT GCCGTGGGCG ACGCACTGGA GAAGGTCTGT 300
AACGAGATCA AGATAGTGGC AGCCCCTGAT GGAGGATCCA TCTTGAAGAT CAGCAACAAG 360
TTCCACACCA AAGGCGACCA TGAGATAAAT GCAGAGCAGA TTAAGATTGA AAAAGAAAAG 420
GCCGTGGGAC TTCTCAAGGC CGTTGAGAGC TACCTCTTGG CACACTCTGA TGCCTACAAC 480
```

( 2 ) INFORMATION FOR SEQ ID NO:3:

( i ) SEQUENCE CHARACTERISTICS:
( A ) LENGTH: 160 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( A ) ORGANISM: Alder (Alnus sp.)

( x i ) SEQUENCE DESCRIPTION: SEQ ID NO:3:

```
Met Gly Val Phe Asn Tyr Glu Ala Glu Thr Pro Ser Val Ile Pro Ala
1               5                   10                  15

Ala Arg Leu Phe Lys Ala Phe Ile Leu Asp Gly Asp Lys Leu Leu Pro
            20                  25                  30

Lys Val Ala Pro Glu Ala Val Ser Ser Val Glu Asn Ile Glu Gly Asn
        35                  40                  45
```

-continued

```
Gly Gly Pro Gly Thr Ile Lys Lys Ile Thr Phe Pro Glu Gly Ser Pro
    50                  55                  60

Phe Lys Tyr Val Lys Glu Arg Val Asp Glu Val Asp Arg Val Asn Phe
65                  70                  75                  80

Lys Tyr Ser Phe Ser Val Ile Glu Gly Gly Ala Val Gly Asp Ala Leu
                85                  90                  95

Glu Lys Val Cys Asn Glu Ile Lys Ile Val Ala Ala Pro Asp Gly Gly
            100                 105                 110

Ser Ile Leu Lys Ile Ser Asn Lys Phe His Thr Lys Gly Asp His Glu
        115                 120                 125

Ile Asn Ala Glu Gln Ile Lys Ile Glu Lys Glu Lys Ala Val Gly Leu
    130                 135                 140

Leu Lys Ala Val Glu Ser Tyr Leu Leu Ala His Ser Asp Ala Tyr Asn
145                 150                 155                 160
```

( 2 ) INFORMATION FOR SEQ ID NO:4:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: YES ( i x ) FEATURE:
( D ) OTHER INFORMATION: Primer for reverse transcription ( x i ) SEQUENCE DESCRIPTION: SEQ ID NO:4:

```
TTTAATACGA CTCACTATAG ATCTCCCGGG AAGCTTTTTT TTTTTTTTTT        50
```

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: YES ( v i ) ORIGINAL SOURCE:
( C ) INDIVIDUAL ISOLATE: 2482

( i x ) FEATURE:
( D ) OTHER INFORMATION: Primer for polymerase chain reaction (PCR) utilized at the 5' end of Aln g I mRNA ( x i ) SEQUENCE DESCRIPTION: SEQ ID NO:5:

```
GTTTTCAATT ACGAAGCGGA AAC        23
```

( 2 ) INFORMATION FOR SEQ ID NO:6:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: YES ( v i ) ORIGINAL SOURCE:

-continued ( C ) INDIVIDUAL ISOLATE: 2490

( i x ) FEATURE:
( D ) OTHER INFORMATION: Primer for polymerase chain reaction (PCR) utilized at the 5'end of Aln g I mRNA ( x i ) SEQUENCE DESCRIPTION: SEQ ID NO:6:

GTTTTCAATT ACGAAGCGGA GAC 23

( 2 ) INFORMATION FOR SEQ ID NO:7:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: YES ( i x ) FEATURE:
( D ) OTHER INFORMATION: Primer for polymerase chain reaction (PCR) utilized at the 3'end of Aln g I mRNA ( x i ) SEQUENCE DESCRIPTION: SEQ ID NO:7:

AATACGACTC ACTA 14

( 2 ) INFORMATION FOR SEQ ID NO:8:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: YES ( x i ) SEQUENCE DESCRIPTION: SEQ ID NO:8:

CTTCGTAATT GAAAACACCC ATGAATTCCG ATACCGTCGA 40

( 2 ) INFORMATION FOR SEQ ID NO:9:

( i ) SEQUENCE CHARACTERISTICS:
( A ) LENGTH: 619 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:9:

ATGGGTGTTT TCAATTACGA GGTTGAGACT CCCTCCGTTA TCCCTGCGGC AAGGCTGTTC 60

AAGTCCTATG TCCTTGATGG CGATAAGCTC ATCCCAAAGG TTGCACCTCA AGCTATTACC 120

AGCGTTGAAA ACGTTGAAGG AAATGGAGGG CCTGGAACCA TCAAGAATAT CACCTTTGGC 180

GAAGGCAGCC GTTACAAGTA CGTGAAGGAG AGGGTTGATG AGGTTGACAA CACAAACTTC 240

-continued

```
ACATACAGCT ACACCGTGAT CGAGGGTGAT GTCCTGGGTG ACAAGCTGGA GAAGGTCTGC   300
CACGAGCTGA AGATAGTGGC AGCCCCTGGT GGAGGATCCA TCTTGAAGAT CAGCAGCAAG   360
TTCCACGCCA AAGGCGACCA TGAGATTAAT GCAGAGGAGA TGAAGGGTGC CAAAGAAATG   420
GCAGAGAAAC TTTTAAGGGC GGTTGAGACC TACCTATTGG CACACTCTGC TGAATACAAC   480
TAAATATCGT CTTGTGTCTT CGCCCAATAA TAACTTGTAC GTGGCTTTCA TGTTTTTTTT   540
AAAAAACTTT GTTTACTTGC TAATAAAGGA GCTTGCGGTT GTGTTCATCT GCTTGCTGAA   600
AAAAAAAAAA AAAAAAAAA                                                619
```

( 2 ) INFORMATION FOR SEQ ID NO:10:

( i ) SEQUENCE CHARACTERISTICS:
( A ) LENGTH: 480 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:10:

```
ATGGGTGTTT TCAATTACGA GGTTGAGACT CCCTCCGTTA TCCCTGCGGC AAGGCTGTTC    60
AAGTCCTATG TCCTTGATGG CGATAAGCTC ATCCCAAAGG TTGCACCTCA AGCTATTACC   120
AGCGTTGAAA ACGTTGAAGG AAATGGAGGG CCTGGAACCA TCAAGAATAT CACCTTTGGC   180
GAAGGCAGCC GTTACAAGTA CGTGAAGGAG AGGGTTGATG AGGTTGACAA CACAAACTTC   240
ACATACAGCT ACACCGTGAT CGAGGGTGAT GTCCTGGGTG ACAAGCTGGA GAAGGTCTGC   300
CACGAGCTGA AGATAGTGGC AGCCCCTGGT GGAGGATCCA TCTTGAAGAT CAGCAGCAAG   360
TTCCACGCCA AAGGCGACCA TGAGATTAAT GCAGAGGAGA TGAAGGGTGC CAAAGAAATG   420
GCAGAGAAAC TTTTAAGGGC GGTTGAGACC TACCTATTGG CACACTCTGC TGAATACAAC   480
```

( 2 ) INFORMATION FOR SEQ ID NO:11:

( i ) SEQUENCE CHARACTERISTICS:
( A ) LENGTH: 160 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:11:

```
Met Gly Val Phe Asn Tyr Glu Val Glu Thr Pro Ser Val Ile Pro Ala
1               5                   10                  15

Ala Arg Leu Phe Lys Ser Tyr Val Leu Asp Gly Asp Lys Leu Ile Pro
            20                  25                  30
```

-continued

| | | | | | | | | | | | | | | | |
|---|---|---|---|---|---|---|---|---|---|---|---|---|---|---|---|
| Lys | Val | Ala | Pro | Gln | Ala | Ile | Thr | Ser | Val | Glu | Asn | Val | Glu | Gly | Asn |
| | | 35 | | | | | 40 | | | | | 45 | | | |
| Gly | Gly | Pro | Gly | Thr | Ile | Lys | Asn | Ile | Thr | Phe | Gly | Glu | Gly | Ser | Arg |
| | 50 | | | | | 55 | | | | | 60 | | | | |
| Tyr | Lys | Tyr | Val | Lys | Glu | Arg | Val | Asp | Glu | Val | Asp | Asn | Thr | Asn | Phe |
| 65 | | | | | 70 | | | | | 75 | | | | | 80 |
| Thr | Tyr | Ser | Tyr | Thr | Val | Ile | Glu | Gly | Asp | Val | Leu | Gly | Asp | Lys | Leu |
| | | | | 85 | | | | | 90 | | | | | 95 | |
| Glu | Lys | Val | Cys | His | Glu | Leu | Lys | Ile | Val | Ala | Ala | Pro | Gly | Gly | Gly |
| | | | 100 | | | | | 105 | | | | | 110 | | |
| Ser | Ile | Leu | Lys | Ile | Ser | Ser | Lys | Phe | His | Ala | Lys | Gly | Asp | His | Glu |
| | | 115 | | | | | 120 | | | | | 125 | | | |
| Ile | Asn | Ala | Glu | Glu | Met | Lys | Gly | Ala | Lys | Glu | Met | Ala | Glu | Lys | Leu |
| | 130 | | | | | 135 | | | | | 140 | | | | |
| Leu | Arg | Ala | Val | Glu | Thr | Tyr | Leu | Leu | Ala | His | Ser | Ala | Glu | Tyr | Asn |
| 145 | | | | | 150 | | | | | 155 | | | | | 160 |

( 2 ) INFORMATION FOR SEQ ID NO:12:

( i ) SEQUENCE CHARACTERISTICS:
( A ) LENGTH: 742 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:12:

```
ATGGGTGTTT TCAATTACGA GGTTGAGACT CCCTCCGTTA TCCCAGCGGC AAGGCTGTTC    60
AAGTCCTATG TCCTTGATGG CGATAAGCTC ATCCCAAAGG TTGCACCTCA AGCTATTACC   120
AGCGTTGAAA ACGTTGAAGG AAATGGAGGG CCTGGAACCA TCAAGAATAT CACCTTTGGC   180
GAAGGCAGCC GTTACAAGTA CGTGAAGGAG AGGGTTGATG AGGTTGACAA CACAAACTTC   240
AAATATAGCT ACACCGTGAT CGAGGGTGAT GTCCTGGGTG ACAAGCTGGA GAAGGTCTGC   300
AGCGAGCTGA AGATAGTGGC AGCCCCTGGT GGAGGATCCA TCTTGAAGAT CAGCAGCAAG   360
TTCCACGCCA AAGGCGACCA TGAGATTAAT GCAGAGGAGA TGAAGGGTGC CAAAGAAATG   420
GCCGAGAAAC TTTTAAGGGC GGTTGAGACC TACCTATTGG CACACTCTGC TGAATACAAC   480
TAAATATCGT CTTGTGTCTT CGCCCAATAA TAACTTGTAC GTGGCTTTCA TGTTTTTTTT   540
TTAAAACTTT GATTACTTGC TAATAAAGGA GCTTGCGGTT GTGTTCATCT GCTTGCTGAA   600
ATCGATGTTG TAACTCGGAA GAATGCAAAC TGAATGTTGT ATTACTTTTT GCATATATAC   660
AAATAATGGA AAGGATAACA TCATTGAAGT TCAAAAAAAA AAAAAAAAAA AAAAAAAAAA   720
AAAAAAAAAA AAAAAAAAAA AA                                            742
```

( 2 ) INFORMATION FOR SEQ ID NO:13:

( i ) SEQUENCE CHARACTERISTICS:
( A ) LENGTH: 480 base pairs
( B ) TYPE: nucleic acid
( C ) STRANDEDNESS: single -continued ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:13:

```
ATGGGTGTTT TCAATTACGA GGTTGAGACT CCCTCCGTTA TCCCAGCGGC AAGGCTGTTC    60
AAGTCCTATG TCCTTGATGG CGATAAGCTC ATCCCAAAGG TTGCACCTCA AGCTATTACC   120
AGCGTTGAAA ACGTTGAAGG AAATGGAGGG CCTGGAACCA TCAAGAATAT CACCTTTGGC   180
GAAGGCAGCC GTTACAAGTA CGTGAAGGAG AGGGTTGATG AGGTTGACAA CACAAACTTC   240
AAATATAGCT ACACCGTGAT CGAGGGTGAT GTCCTGGGTG ACAAGCTGGA GAAGGTCTGC   300
AGCGAGCTGA AGATAGTGGC AGCCCCTGGT GGAGGATCCA TCTTGAAGAT CAGCAGCAAG   360
TTCCACGCCA AAGGCGACCA TGAGATTAAT GCAGAGGAGA TGAAGGGTGC CAAAGAAATG   420
GCCGAGAAAC TTTTAAGGGC GGTTGAGACC TACCTATTGG CACACTCTGC TGAATACAAC   480
```

( 2 ) INFORMATION FOR SEQ ID NO:14:

( i ) SEQUENCE CHARACTERISTICS:
( A ) LENGTH: 160 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:14:

```
Met Gly Val Phe Asn Tyr Glu Val Glu Thr Pro Ser Val Ile Pro Ala
 1               5                  10                  15

Ala Arg Leu Phe Lys Ser Tyr Val Leu Asp Gly Asp Lys Leu Ile Pro
            20                  25                  30

Lys Val Ala Pro Gln Ala Ile Thr Ser Val Glu Asn Val Glu Gly Asn
        35                  40                  45

Gly Gly Pro Gly Thr Ile Lys Asn Ile Thr Phe Gly Glu Gly Ser Arg
    50                  55                  60

Tyr Lys Tyr Val Lys Glu Arg Val Asp Glu Val Asp Asn Thr Asn Phe
65                  70                  75                  80

Lys Tyr Ser Tyr Thr Val Ile Glu Gly Asp Val Leu Gly Asp Lys Leu
                85                  90                  95

Glu Lys Val Cys Ser Glu Leu Lys Ile Val Ala Ala Pro Gly Gly Gly
            100                 105                 110

Ser Ile Leu Lys Ile Ser Ser Lys Phe His Ala Lys Gly Asp His Glu
        115                 120                 125

Ile Asn Ala Glu Glu Met Lys Gly Ala Lys Glu Met Ala Glu Lys Leu
    130                 135                 140

Leu Arg Ala Val Glu Thr Tyr Leu Leu Ala His Ser Ala Glu Tyr Asn
```

145 150 155 160

( 2 ) INFORMATION FOR SEQ ID NO:15:

( i ) SEQUENCE CHARACTERISTICS:
( A ) LENGTH: 655 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:15:

```
ATGGGTGTTT TCAATTACGA GGCTGAGACC ACCTCCGTTA TCCCTGCGGC AAGGCTGTTC    60
AAGTCCTATG TCCTTGATGG CGATAAGCTC ATCCCAAAGG TTGCACCTCA AGCTATTACC   120
AGCGTTGAAA ACGTTGAAGG AAATGGAGGG CCTGGAACCA TCAAGAATAT CACCTTTGGC   180
GAAGGCAGCC GTTACAAGTA CGTGAAGGAG AGGGTTGATG AGGTTGACAA CACAAACTTC   240
ACATACAGCT ACACCGTGAT CGAGGGTGAT GTCCTGGGTG ACAAGCTGGA GAAGGTCTGC   300
CACGAGCTGA AGATAGTGGC AGCCCCTGGT GGAGGATCCA TCTTGAAGAT CAGCAGCAAG   360
TTCCACGCCA AAGGTGACCA TGAGATTAAT GCAGAGGAGA TGAAGGGTGC CAAAGAAATG   420
GCCGAGAAAC TTTTAAGGGC GGTTGAGACC TACCTATTGG CACACTCTGC TGAATACAAC   480
TAAACCTCGT CTTGTGTCTT CGCCCAATAA TAGCTTGTAC GTGGCTTTCA TGTTTTTTTT   540
TTAAACTTTG TTTTCTTGCT AATAAAGGAG CTTGCGGTTG TGTTCATCTG CTTGCTGAAG   600
ATCGATGTTG TAACTCGGAA GAATGCAAAT TTAATGTTGT ATTAAAAAAA AAAAA        655
```

( 2 ) INFORMATION FOR SEQ ID NO:16:

( i ) SEQUENCE CHARACTERISTICS:
( A ) LENGTH: 480 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:16:

```
ATGGGTGTTT TCAATTACGA GGCTGAGACC ACCTCCGTTA TCCCTGCGGC AAGGCTGTTC    60
AAGTCCTATG TCCTTGATGG CGATAAGCTC ATCCCAAAGG TTGCACCTCA AGCTATTACC   120
AGCGTTGAAA ACGTTGAAGG AAATGGAGGG CCTGGAACCA TCAAGAATAT CACCTTTGGC   180
GAAGGCAGCC GTTACAAGTA CGTGAAGGAG AGGGTTGATG AGGTTGACAA CACAAACTTC   240
ACATACAGCT ACACCGTGAT CGAGGGTGAT GTCCTGGGTG ACAAGCTGGA GAAGGTCTGC   300
```

-continued

| | | | | | | |
|---|---|---|---|---|---|---|
| CACGAGCTGA | AGATAGTGGC | AGCCCCTGGT | GGAGGATCCA | TCTTGAAGAT | CAGCAGCAAG | 360 |
| TTCCACGCCA | AAGGTGACCA | TGAGATTAAT | GCAGAGGAGA | TGAAGGGTGC | CAAAGAAATG | 420 |
| GCCGAGAAAC | TTTTAAGGGC | GGTTGAGACC | TACCTATTGG | CACACTCTGC | TGAATACAAC | 480 |

( 2 ) INFORMATION FOR SEQ ID NO:17:

( i ) SEQUENCE CHARACTERISTICS:
( A ) LENGTH: 160 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:17:

Met Gly Val Phe Asn Tyr Glu Ala Glu Thr Thr Ser Val Ile Pro Ala
1 5 10 15

Ala Arg Leu Phe Lys Ser Tyr Val Leu Asp Gly Asp Lys Leu Ile Pro
20 25 30

Lys Val Ala Pro Gln Ala Ile Thr Ser Val Glu Asn Val Glu Gly Asn
35 40 45

Gly Gly Pro Gly Thr Ile Lys Asn Ile Thr Phe Gly Glu Gly Ser Arg
50 55 60

Tyr Lys Tyr Val Lys Glu Arg Val Asp Glu Val Asp Asn Thr Asn Phe
65 70 75 80

Thr Tyr Ser Tyr Thr Val Ile Glu Gly Asp Val Leu Gly Asp Lys Leu
85 90 95

Glu Lys Val Cys His Glu Leu Lys Ile Val Ala Ala Pro Gly Gly Gly
100 105 110

Ser Ile Leu Lys Ile Ser Ser Lys Phe His Ala Lys Gly Asp His Glu
115 120 125

Ile Asn Ala Glu Glu Met Lys Gly Ala Lys Glu Met Ala Glu Lys Leu
130 135 140

Leu Arg Ala Val Glu Thr Tyr Leu Leu Ala His Ser Ala Glu Tyr Asn
145 150 155 160

( 2 ) INFORMATION FOR SEQ ID NO:18:

( i ) SEQUENCE CHARACTERISTICS:
( A ) LENGTH: 860 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:18:

| | | | | | | |
|---|---|---|---|---|---|---|
| ATGGGTGTTT | TCAATTACGA | GGTTGAGACC | CCCTCCGTTA | TCTCAGCGGC | AAGGCTGTTC | 60 |

-continued

AAGTCCTATG TCCTTGATGG CGATAAGCTC ATCCCAAAGG TTGCACCTCA AGCTATTACC 120

AGCGTTGAAA ACGTTGGAGG AAATGGAGGG CCTGGAACCA TCAAGAATAT CACCTTTGGC 180

GAAGGCAGCC GTTACAAGTA CGTGAAGGAG AGGGTTGATG AGGTTGACAA CACAAACTTC 240

AAATATAGCT ACACCGTGAT CGAGGGTGAT GTCCTGGGTG ACAAGCTGGA GAAAGTCTGC 300

AGCGAGCTGA AGATAGTGGC AGCCCCTGGT GGGGGATCCA CCTTGAAGAT CAGCAGCAAG 360

TTCCACGCCA AAGGTGACCA TGAGATTAAT GCAGAGGAGA TGAAGGGTGC CAAAGAAATG 420

GCCGAGAAAC TTTTAAGGGC GGTTGAGACC TACCTATTGG CACACTCTGC TGAATACAAC 480

TAAATATCGT CTTGTGTCTT CGCCAATAAT AACTTGTACG TGGCTTTCAT GTTTTTTTTT 540

AAAAAACTTT GTTTACTTGC TAATAAAGGA GCTTGCGGTT GTGTTCATCT GCTTGCTGAA 600

ATCGATGTTG TAACTCGGAA GAATGCAAAC TGAATGTTGT ATTACTTTTT GCATATATAC 660

AAATAATGGA AAGGATAACA TCATTGAAGT TCAAAAAAAA GAAAAAAAAA AGCTTTTTTT 720

TTTTTTTTTT TTTTTTTTTT TTTTTTGTCA ATTTTAACCC GATACTGATA CTCAAAAATG 780

CAAGAGAGTT TCCGCATAAG CACAATTTGT TTATGTTGAC TTAATACATT ATAAGCAAAA 840

AAAAAAAAAA AAAAAAAAAA 860

( 2 ) INFORMATION FOR SEQ ID NO:19:

( i ) SEQUENCE CHARACTERISTICS:
( A ) LENGTH: 480 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:19:

ATGGGTGTTT TCAATTACGA GGTTGAGACC CCCTCCGTTA TCTCAGCGGC AAGGCTGTTC 60

AAGTCCTATG TCCTTGATGG CGATAAGCTC ATCCCAAAGG TTGCACCTCA AGCTATTACC 120

AGCGTTGAAA ACGTTGGAGG AAATGGAGGG CCTGGAACCA TCAAGAATAT CACCTTTGGC 180

GAAGGCAGCC GTTACAAGTA CGTGAAGGAG AGGGTTGATG AGGTTGACAA CACAAACTTC 240

AAATATAGCT ACACCGTGAT CGAGGGTGAT GTCCTGGGTG ACAAGCTGGA GAAAGTCTGC 300

AGCGAGCTGA AGATAGTGGC AGCCCCTGGT GGGGGATCCA CCTTGAAGAT CAGCAGCAAG 360

TTCCACGCCA AAGGTGACCA TGAGATTAAT GCAGAGGAGA TGAAGGGTGC CAAAGAAATG 420

GCCGAGAAAC TTTTAAGGGC GGTTGAGACC TACCTATTGG CACACTCTGC TGAATACAAC 480

( 2 ) INFORMATION FOR SEQ ID NO:20:

( i ) SEQUENCE CHARACTERISTICS:
( A ) LENGTH: 160 amino acids
( B ) TYPE: amino acid
( D ) TOPOLOGY: linear ( i i ) MOLECULE TYPE: peptide ( i i i ) HYPOTHETICAL: NO -continued ( v i ) ORIGINAL SOURCE:
( A ) ORGANISM: hazel (Corylus sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:20:

| | | | | | | | | | | | | | | | |
|---|---|---|---|---|---|---|---|---|---|---|---|---|---|---|---|
| Met | Gly | Val | Phe | Asn | Tyr | Glu | Val | Glu | Thr | Pro | Ser | Val | Ile | Ser | Ala |
| 1 | | | | 5 | | | | | 10 | | | | | 15 | |
| Ala | Arg | Leu | Phe | Lys | Ser | Tyr | Val | Leu | Asp | Gly | Asp | Lys | Leu | Ile | Pro |
| | | | 20 | | | | | 25 | | | | | 30 | | |
| Lys | Val | Ala | Pro | Gln | Ala | Ile | Thr | Ser | Val | Glu | Asn | Val | Gly | Gly | Asn |
| | | 35 | | | | | 40 | | | | | 45 | | | |
| Gly | Gly | Pro | Gly | Thr | Ile | Lys | Asn | Ile | Thr | Phe | Gly | Glu | Gly | Ser | Arg |
| | 50 | | | | | 55 | | | | | 60 | | | | |
| Tyr | Lys | Tyr | Val | Lys | Glu | Arg | Val | Asp | Glu | Val | Asp | Asn | Thr | Asn | Phe |
| 65 | | | | | 70 | | | | | 75 | | | | | 80 |
| Lys | Tyr | Ser | Tyr | Thr | Val | Ile | Glu | Gly | Asp | Val | Leu | Gly | Asp | Lys | Leu |
| | | | | 85 | | | | | 90 | | | | | 95 | |
| Glu | Lys | Val | Cys | Ser | Glu | Leu | Lys | Ile | Val | Ala | Ala | Pro | Gly | Gly | Gly |
| | | | 100 | | | | | 105 | | | | | 110 | | |
| Ser | Thr | Leu | Lys | Ile | Ser | Ser | Lys | Phe | His | Ala | Lys | Gly | Asp | His | Glu |
| | | 115 | | | | | 120 | | | | | 125 | | | |
| Ile | Asn | Ala | Glu | Glu | Met | Lys | Gly | Ala | Lys | Glu | Met | Ala | Glu | Lys | Leu |
| | 130 | | | | | 135 | | | | | 140 | | | | |
| Leu | Arg | Ala | Val | Glu | Thr | Tyr | Leu | Leu | Ala | His | Ser | Ala | Glu | Tyr | Asn |
| 145 | | | | | 150 | | | | | 155 | | | | | 160 |

( 2 ) INFORMATION FOR SEQ ID NO:21:

( i ) SEQUENCE CHARACTERISTICS:
( A ) LENGTH: 672 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: birch (Betula sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:21:

ATGGGTGTTT TCAATTACGA AACTGAGACC ACCTCTGTTA TCCCAGCAGC TCGACTGTTC 60

AAGGCCTTTA TCCTTGATGG CGATAATCTC TTTCCAAAGG TTGCACCCCA AGCCATTAGC 120

AGTGTTGAAA ACATTGAAGG AAATGGAGGG CCTGGAACCA TTAAGAAGAT CAGCTTTCCC 180

GAAGGCTTCC CTTTCAAGTA CGTGAAGGAC AGAGTTGATG AGGTGGACCA CACAAACTTC 240

AAATACAATT ACAGCGTGAT CGAGGGCGGT CCCATAGGCG ACACATTGGA GAAGATCTCC 300

AACGAGATAA AGATAGTGGC AACCCCTGAT GGAGGATCCA TCTTGAAGAT CAGCAACAAG 360

TACCACACCA AAGGTGACCA TGAGGTGAAG GCAGAGCAGG TTAAGGCAAG TAAAGAAATG 420

GGCGAGACAC TTTTGAGGGC CGTTGAGAGC TACCTCTTGG CACACTCCGA TGCCTACAAC 480

TAATTAATTA ACTTGTGTCG TCTCGAACAT GTCCCTGATC AATAATGGGT TGCAGTGTTC 540

ATGGTGTTTT TTGGGTCTAA TAAAGGAGCT TGCAGTTGTG ATCATCTGCT TGCTAGCTGA 600

AGATGTTGTA ATTTATTGGG AGAATGATAA TAAATGTTCT ATTAAAAAAA AAAAAAAAAA 660

AAAAAAAAAA AA 672

( 2 ) INFORMATION FOR SEQ ID NO:22:

( i ) SEQUENCE CHARACTERISTICS:
( A ) LENGTH: 480 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: birch (Betula sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:22:

ATGGGTGTTT TCAATTACGA AACTGAGACC ACCTCTGTTA TCCCAGCAGC TCGACTGTTC 60

AAGGCCTTTA TCCTTGATGG CGATAATCTC TTTCCAAAGG TTGCACCCCA AGCCATTAGC 120

AGTGTTGAAA ACATTGAAGG AAATGGAGGG CCTGGAACCA TTAAGAAGAT CAGCTTTCCC 180

GAAGGCTTCC CTTTCAAGTA CGTGAAGGAC AGAGTTGATG AGGTGGACCA CACAAACTTC 240

AAATACAATT ACAGCGTGAT CGAGGGCGGT CCCATAGGCG ACACATTGGA GAAGATCTCC 300

AACGAGATAA AGATAGTGGC AACCCCTGAT GGAGGATCCA TCTTGAAGAT CAGCAACAAG 360

TACCACACCA AAGGTGACCA TGAGGTGAAG GCAGAGCAGG TTAAGGCAAG TAAAGAAATG 420

GGCGAGACAC TTTTGAGGGC CGTTGAGAGC TACCTCTTGG CACACTCCGA TGCCTACAAC 480

( 2 ) INFORMATION FOR SEQ ID NO:23:

( i ) SEQUENCE CHARACTERISTICS:
( A ) LENGTH: 160 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( A ) ORGANISM: birch (Betula sp.)

( v i i ) IMMEDIATE SOURCE:
( A ) LIBRARY: POLLEN FROM ALLERGON AB, ENGELHOLM, SWEDEN ( x i ) SEQUENCE DESCRIPTION: SEQ ID NO:23:

Met Gly Val Phe Asn Tyr Glu Thr Glu Thr Thr Ser Val Ile Pro Ala
1 5 10 15

Ala Arg Leu Phe Lys Ala Phe Ile Leu Asp Gly Asp Asn Leu Phe Pro
20 25 30

Lys Val Ala Pro Gln Ala Ile Ser Ser Val Glu Asn Ile Glu Gly Asn
35 40 45

Gly Gly Pro Gly Thr Ile Lys Lys Ile Ser Phe Pro Glu Gly Phe Pro
50 55 60

Phe Lys Tyr Val Lys Asp Arg Val Asp Glu Val Asp His Thr Asn Phe
65 70 75 80

Lys Tyr Asn Tyr Ser Val Ile Glu Gly Gly Pro Ile Gly Asp Thr Leu

-continued

| | | | | | | | | | | | | | | | |
|---|---|---|---|---|---|---|---|---|---|---|---|---|---|---|---|
| | | | | 85 | | | | | 90 | | | | | 95 | |
| Glu | Lys | Ile | Ser | Asn | Glu | Ile | Lys | Ile | Val | Ala | Thr | Pro | Asp | Gly | Gly |
| | | | 100 | | | | | 105 | | | | | 110 | | |
| Ser | Ile | Leu | Lys | Ile | Ser | Asn | Lys | Tyr | His | Thr | Lys | Gly | Asp | His | Glu |
| | | 115 | | | | | 120 | | | | | 125 | | | |
| Val | Lys | Ala | Glu | Gln | Val | Lys | Ala | Ser | Lys | Glu | Met | Gly | Glu | Thr | Leu |
| | 130 | | | | | 135 | | | | | 140 | | | | |
| Leu | Arg | Ala | Val | Glu | Ser | Tyr | Leu | Leu | Ala | His | Ser | Asp | Ala | Tyr | Asn |
| 145 | | | | | 150 | | | | | 155 | | | | | 160 |